United States Patent [19]

Stephen et al.

[11] Patent Number: 4,652,093
[45] Date of Patent: Mar. 24, 1987

[54] OPTICAL INSTRUMENTS

[75] Inventors: Richard O. Stephen, Oadby; Colin D. Ockleford, Market Harborough, both of England

[73] Assignee: Gwyndann Group Limited, Cambridgeshire, England

[21] Appl. No.: 552,444

[22] Filed: Nov. 16, 1983

[30] Foreign Application Priority Data

Nov. 19, 1982 [GB] United Kingdom ................. 8233132
Nov. 19, 1982 [GB] United Kingdom ................. 8233133

[51] Int. Cl.[4] .................................... G02B 27/64
[52] U.S. Cl. .................................... 350/500
[58] Field of Search ............... 128/4, 746; 350/523, 350/526, 527, 528; 356/23; 372/25, 29, 30

[56] References Cited

U.S. PATENT DOCUMENTS

| 3,585,520 | 6/1971 | Yanai et al. | 372/25 |
| 3,867,764 | 2/1975 | Dunmire et al. | 362/800 |
| 4,185,891 | 1/1980 | Kaestner | 362/800 |
| 4,241,251 | 12/1980 | Yonekubo | 350/526 |
| 4,351,584 | 9/1982 | Chandesais | 350/523 |
| 4,467,193 | 8/1984 | Carroll | 362/800 |
| 4,501,961 | 2/1985 | Stauffer | 250/560 |

FOREIGN PATENT DOCUMENTS

| 2408765 | 9/1975 | Fed. Rep. of Germany | 128/746 |
| 2099999 | 12/1982 | United Kingdom | 128/746 |

OTHER PUBLICATIONS

Dawe Dig. (G.B.) vol. 13, No. 2 (Jun. 1970), *Throwing New Light on Microscopy*.
Andrews et al., *Light Emitting Diode as a Short-Duration Stroboscope-Application to Visualization of Ultrasound*, Jan. 1977, Journal of Physics E, vol. 10, No. 1, p. 95.

Primary Examiner—John K. Corbin
Assistant Examiner—Vincent J. Lemmo
Attorney, Agent, or Firm—Charles E. Brown; Charles A. Brown

[57] ABSTRACT

The invention relates to the illumination of optical instruments such as microscopes or auriscopes by means of the light from light-emitting diodes (L.E.D.) (6, 50). Advantageously, the light from the diodes may be strobed. Examples described include the positioning of L.E.D.'s (6) at the focal point of the inverted condenser lens (2) of a microscope, and the inclusion of a plurality of L.E.D.'s (50) in the probe portion (38) of an auriscope. In the latter case, the device may also be provided with a source of frequency-controlled sound (28) channelled through the probe portion (38).

10 Claims, 10 Drawing Figures

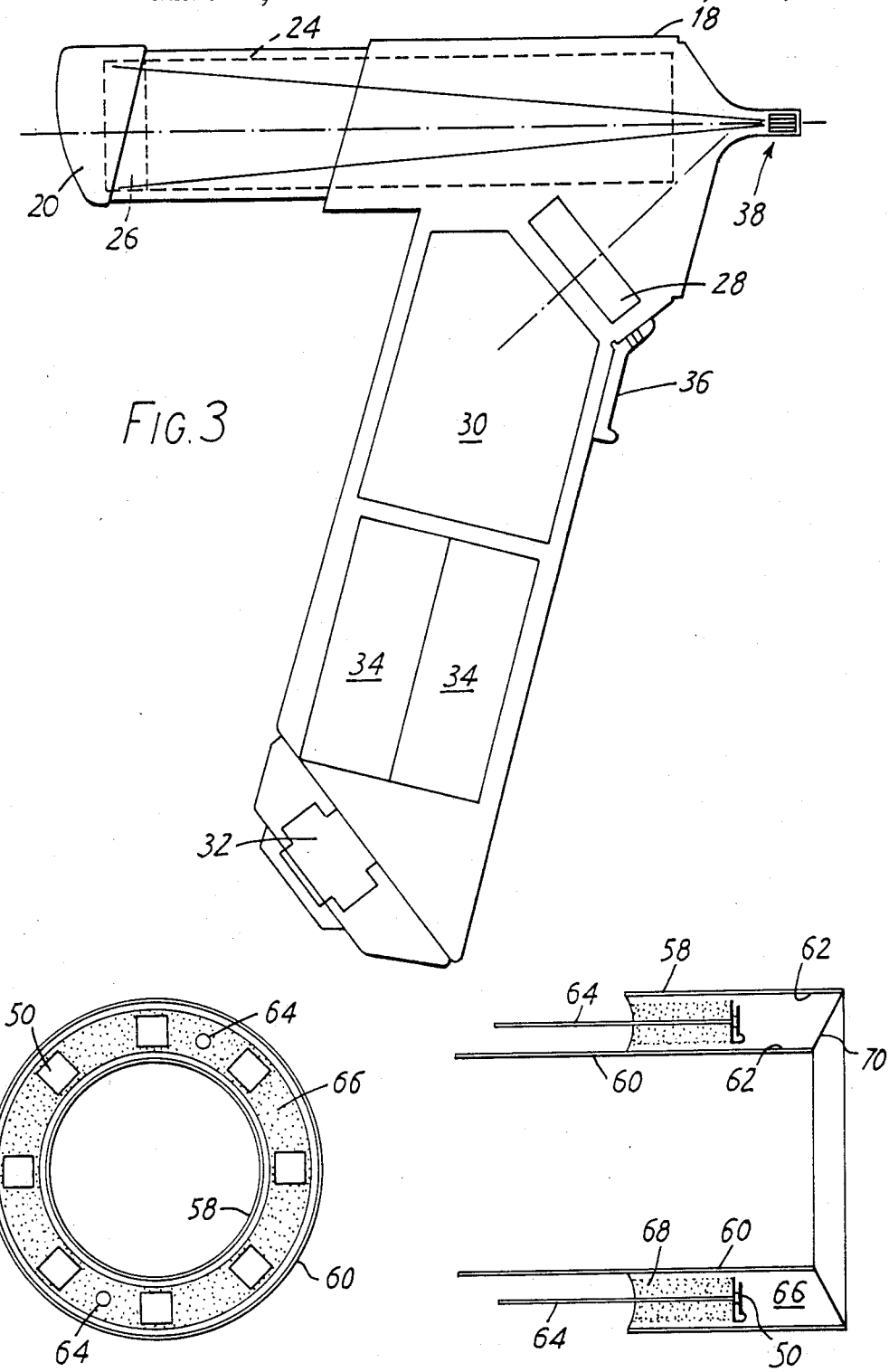

OPTICAL INSTRUMENTS

BACKGROUND OF INVENTION

The invention is concerned with improvements in or relating to optical instruments and particularly to the provision of illumination therefor.

In conventional optical instruments, such as for example optical microscopes, the illumination is provided by a lamp using for example a tungsten filament bulb or other similar source having a spreading pattern of light emission. Although means are available to direct the path of the emitted light, e.g. reflective surfaces, condenser lenses and the like, only a portion of the available light is actually used to give the required illumination to the object to be viewed by the optical apparatus.

Moreover, most light sources generate heat and steps must be taken to dissipate the excess heat, by for example the use of cooling vanes, to avoid damage not only to the instrument but also to the object being viewed.

As a result of this, it is usual for the light source for an optical apparatus arrangement to be a disproportionately large part of the whole arrangement, requiring the instrument to be much more bulky than the optical system itself requires, and to involve the use of a sizable voltage supply and current consumption, yet giving a much lower performance than may be required.

One solution which has been offered to the problem of bulk and dissipation of heat from a source close to the optical viewing region has been to lead light from a conventional source to the viewing region through an optical fibre system, but this does not avoid the problem altogether, merely distancing it slightly. In doing so, the efficiency of light utilisation is not improved.

It is an object of the present invention to minimise the above outlined disadvantages.

BRIEF SUMMARY OF INVENTION

The invention provides in accordance with one of its several aspects, an optical instrument device capable of permitting viewing of an object or an image thereof, said device comprising an illumination source for providing illumination to assist said viewing, said source being a light emitting diode.

The invention further provides a device as described in the preceding paragraph in which means are provided for deflecting the light emitted from the diode to produce a parallel or substantially parallel beam. In examples of devices according to the invention, the means may comprise focussing devices such as the condenser lens of a microscope or alternatively reflective surfaces may be used.

The invention still further provides, in another of its several aspects, a device as described in either of the last two paragraphs in which means are provided to cause the diode source to emit light in a stroboscopic manner.

By way of example, the use of light-emitting diodes as sources of illumination for optical instruments has been found to be notably advantageous in the field of stroboscopic microscopy. Here, the problem of adequate levels of illumination when using conventional lighting sources are worsened by the light loss due to the stroboscopic operation. Thus, where stroboscopic illumination for use with a microscope is provided by for example a xenon discharge tube the area from which light is emitted may be of the region of 20 cm$^2$. Indeed, increasing the area of emitting light means that the proportion of usable light decreases. Moreover, the light output from such a discharge tube is dependent on the flash rate. An example of a commercially available tube gives a light output of 100 lux at 1800 flashes/minute which reduces to only 50 lux at 18,000 flashes/minute.

Xenon discharge tubes require a large voltage, in excess of 100 volts, and large amounts of heat require to be dissipated. Because the nature of the optical path requires the lamp to be largely enclosed, bulky lamp housings have to be provided which include heat-dissipating surfaces and provision for good air circulation. Moreover, a xenon tube cannot be used for continuous illumination needed for normal microscopy and therefore a secondary illumination source is also necessary, for example a standard tungsten filament bulb. Because a light-emitting diode (L.E.D.) is capable of producing continuous as well as intermittent light, a single source of illumination is all that is required, thus avoiding the need for optical realignment when the mode of operation is changed.

Moreover, the electronic control for the switching of the standard stroboscopic discharge tubes produces a constant width voltage pulse. This is the reason for the decrease in light output, mentioned above, when the flash rate is increased. When using a L.E.D. light source, the control circuit may include a variable pulse-width module, thus obviating the problem. Moreover, extremely high switching rates are possible, which make for controllable light pulse profiles. This also makes possible the variation, not only of pulse widths, but pulse rates, to optimise illuminating conditions.

Another example of the varied uses in which the invention may be applied is in the improvement of illuminating conditions in the examination of patients suffering from hearing disorders. Hitherto a conventional auriscope is only of restricted use due to the small dimensions of a patient's external auditory channel (meatus) and detailed observation of the condition or performance of the ear-drum (tympanum) has not been feasible.

The invention therefore provides in another of its several aspects, an optical instrument device capable of permitting viewing of an object, said device being suitable for use as an auriscope and comprising an illumination source for providing illumination to assist said viewing, wherein the source is at least one light-emitting diode, means being provided so as to permit illumination of the tympanum of an ear, and means for rendering the light intermittent in a stroboscopic manner for observing vibratory movement in the tympanum in response to sound.

Advantageously, the optical instrument device or auriscope may comprise a housing including an illumination source comprising at least one light-emitting diode, a leading probe portion having a substantially tubular configuration, means to provide sound at known frequencies to the probe portion, which probe portion affords an inspection passage for the tympanum (eardrum) communicating with said housing and means to direct light from said illumination source, in use, onto a tympanum, and means for rendering the light from said source intermittent in a stroboscopic manner.

Whereas with the use of conventional auriscopes it is not easy to observe the movement of the eardrum therefore a medical practitioner is unable to assess its mechanical function, or malfunction, with the use of the invention it is now possible to observe the eardrum in motion and to assess its vibration characteristics, including the resonant frequency, the compliance of the eardrum, and to measure the Q factor of drum resonance. Thus a deterioration in the elasticity of the drum may be noted, or an excess of damping the resonance of the drum causing an inefficient transfer of sound to the auditory ossicles of the middle ear. With these observations, a practitioner may then be able to asses the likely functional condition of the ossicular chain.

BRIEF DESCRIPTION OF DRAWINGS

There will now be described two examples of optical devices according to the invention. It will be understood that the description which is to be read with reference to the drawings is given by way of example only and not by way of limitation.

In the drawings:

FIG. 3 is schematic side view of a second example comprising an auriscope;

FIG. 4 is an end view of an illumination source of the auriscope of FIG. 3 to a greatly enlarged scale;

FIG. 5 is a side view of the illumination source of FIG. 4;

DETAILED DESCRIPTION OF DRAWINGS

Figure 1:
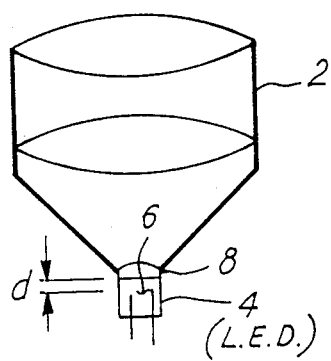
FIG. 1 illustrates diagrammatically a first example in which an inverted condenser lens of a microscope is provided with an illumination source according to the invention.

The first example to be described comprises an optical microscope having a condenser lens arrangement 2 arranged to provide a parallel light beam from a source comprising a light-emitting diode 4 (L.E.D.). In the example the condenser lens system 2 has been inverted compared with its normal orientation and the L.E.D. 4 secured thereto so that the light emission surface 6 thereof lies exactly at the focal point of the lens. It is thus necessary to ensure that the correct distance d exists between the surface 6 and the bond 8 between the methacrylate body of potting material enclosing the diode and the confronting surface of the lens 2. This bond 8 is achieved by an adhesive having a suitable refractive index, in the present example, Canada balsam.

It is thus frequently necessary, as has been the case in the present example, to machine the potting body until the correct value of d has been obtained, so that the parallel beam of light produced can be focussed in the usual way.

Figure 2:
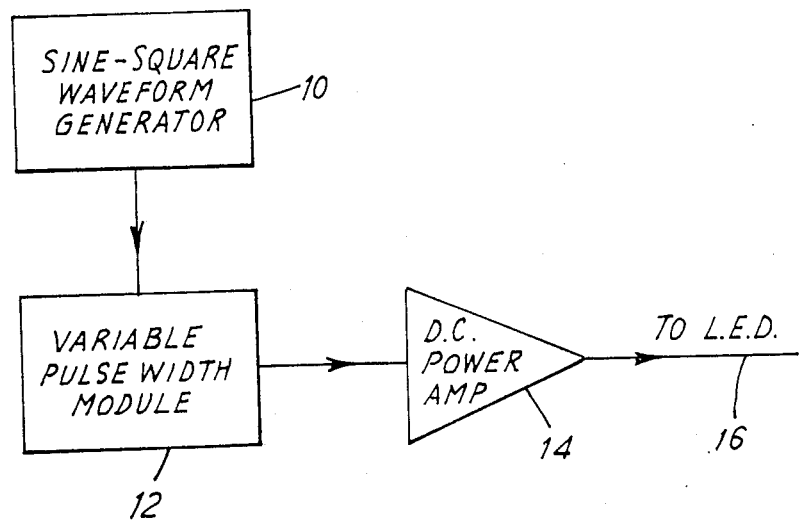
FIG. 2 is a simplified circuit diagram of the electronic control arrangement for the illumination source of the arrangement shown in FIG. 1.

The control circuitry is indicated in FIG. 2 where a sine-square waveform generator 10 is selected for generating the desired frequencies over a wide range, the generator in the present example being a conventional unit with a range of 1 Hz to 10 kHz. The width of the pulse produced may be varied, as mentioned above, using a variable pulse-width module, 12, in the present example, a commercially available unit Neurolog NL 403. A conventional DC power amplifier directs power to the L.E.D. 4 through lead 16. More than one L.E.D. may of course be used in combination.

Such a microscope as described above has many applications, producing an optical performance not hitherto possible. One such use is in the observation of the motility of sperm, in which the beat frequency of the sperm flagellum may be measured using a calibrated, variable frequency stroboscopic microscope and observing spermatazoa using phase contrast microscopy, comparing the results with the normal value at a predetermined temperature and under the appropriate physiological conditions.

Apparatus according to the invention are suitable for phase contrast, interference contrast, differential interference contrast and polarising microscopy, for a wide variety of observations. Besides biological and medical applications, including living tissue examination where the cool running of the L.E.D. illumination removes the risk of burning the tissue, the invention finds use in, for example, the field of textiles in the measurement of yarn filaments or other small diameter fibre material. A sample of a fibre to be examined may be mounted at one end thereof and the free end caused to oscillate in a controlled sound field. The oscillations are characteristic of the type of fibre being examined, for example a polymeric fibre, and in this way, accurate quantitative determination of the flexural strength of the fibre may be made.

A further illustration of the versatility of L.E.D. illuminated microscopy results from the ability to obtain light of differing wavelength by selection of operting current and of the type of L.E.D. used, so as to be able to provide illumination of a required colour. For example, if a cytogeneticist is examining a chromosome preparation which has been stained red by orcein, it is best examined by a green light for maximum image contrast. If white light is desired, this may be achieved by the combination of several L.E.D.'s.

The construction of a microscope using the present invention may be appreciably more robust than is the case with a conventional microscope, or stroboscope. Thus it may be readily used "in the field", operating from small dry cell batteries easily transported on expeditions and unharmed by relatively rough usage. Even under extreme conditions, the L.E.D.'s may be expected to have a long service life compared with conventional light sources.

Because of the low current use, it is particularly advantageous in the context of children's microscopes where the power source may be a torch battery. Such a microscope is nevertheless provided with an illumination system which is a point source precision focussing system. In other contexts, the L.E.D. may simply be used as a surface illuminator, perhaps immersed in a fluid surrounding a specimen.

The second example of an optical instrument to be described is an auriscope.

The auriscope comprises a housing 18, readily held in the hand, and having an eyepiece 20 for a microscope tube 24, which in use is extendible from the housing 18. Adjacent the eyepiece at one end of the microscope tube is a lens system 26. Also received within the housing 18 for purposes which will become apparent are an audio transducer 28, a trimmer and switch device 30 (circuit board) for illumination and sound, and a frequency control potentiometer 32. Two re-chargeable batteries 34 power the auriscope in the present example. An on-off switch 36 is also provided.

Figure 6:
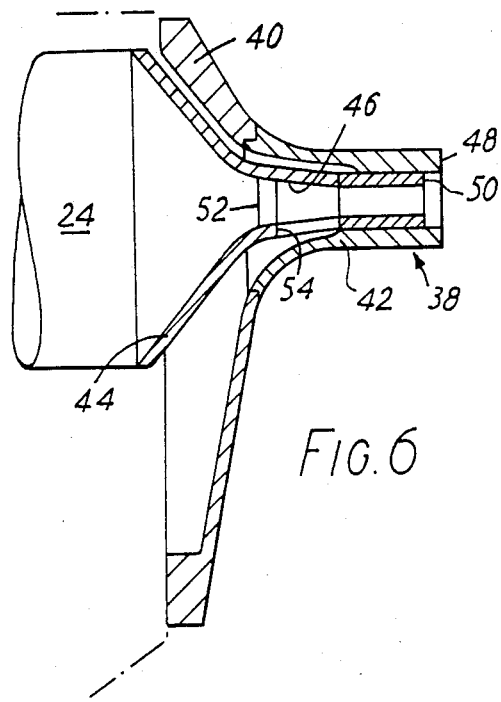
FIG. 6 is a fragmentary view of a part of the auriscope of FIG. 3 to a somewhat enlarged scale.

Arranged at an end portion of the microscope tube 24 remote from the eye-piece 20 is a probe portion 38, shown in greater detail in FIG. 6. The probe portion comprises an external, contoured casing 40 and a removable speculum 42. Within the probe portion is an inner wall member 44 defining a tapering passage 46, the narrowest diameter of which is adjacent an end face 48 of the probe portion. Received within the narrowest diameter of the probe portion is an annular array of light-emitting diodes 50, to be described in detail with reference to FIG. 4 and 5. The interior portion of the passageway 46 is sealed by a clear end plate, 52, of glass or Perspex (R.T.M.). The wall member 44 within the passageway is provided with an opening 54 providing communication through the lower portion of the hollow casing 40 to receive adjustable frequency sound directed towards the patient's eardrum along a path passing axially through the annular array of light emitting diodes 50.

Figure 8:
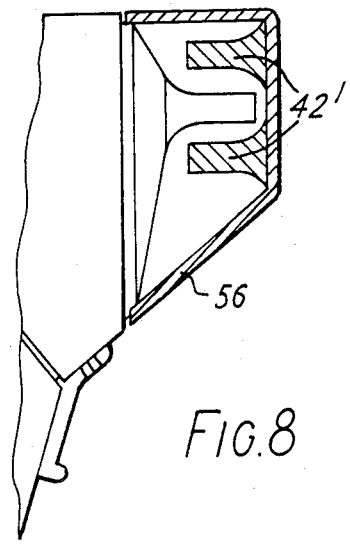
FIG. 8 is a fragmentary view in cross section of a cap-member of the auriscope of FIG. 3.
Figure 7:
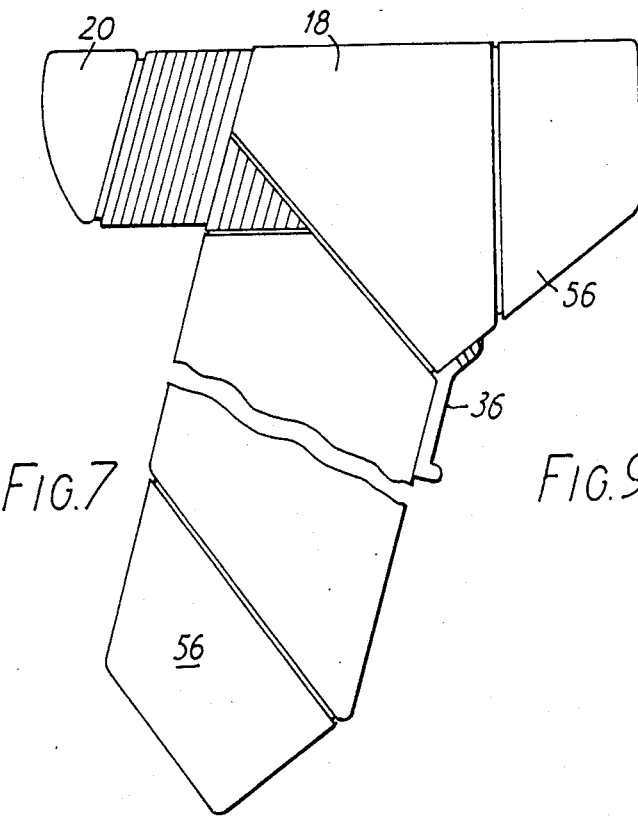
FIG. 7 shows the external features of the auriscope of FIG. 3.
Figure 9:
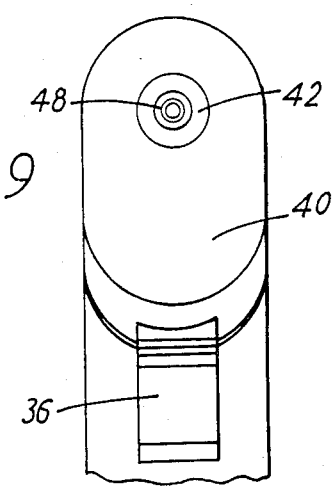
FIG. 9 is a fragmentary end view of the auriscope of FIG. 3.

FIG. 7 shows an end cap 56 fitted upon the housing 18 to protect the probe portion. It will be observed that the cap 56 may be fitted in use in an out-of-the-way position on the housing adjacent the frequency control potentiometer 32. The end cap 56 may conveniently be used to store replacement specula 42', (FIG. 8).

The annular array of L.E.D's will now be described. Eight high-intensity L.E.D.'s 50, are arranged within the annular space between two coaxially arranged stainless steel tubes 58, 60 confronting faces 62 of which have a light-reflective surface. Each diode 50 is connected to a power lead 64 and the arrangement is potted in clear methacrylate material 66 forward of the diodes 50 (to the right as viewed in the drawings), and backfill material 68 is provided behind the diodes. A single element Fresnel lens 70 assists in directing light from the diodes.

Figure 10:
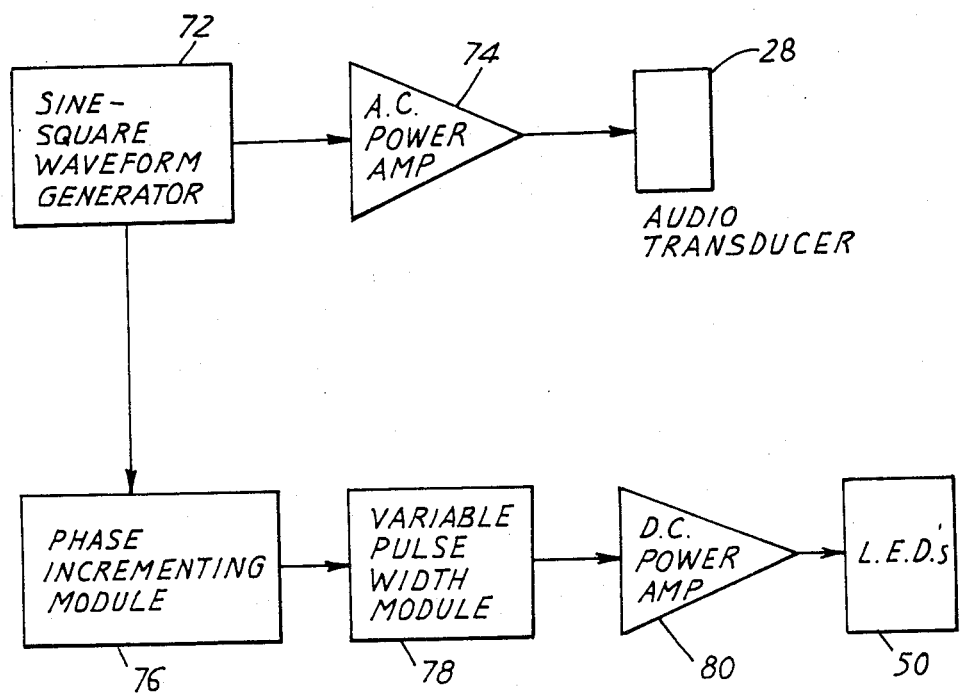
FIG. 10 is a simplified circuit diagram of the electronic control arrangement for the auriscope of FIG. 3.

The circuit diagram of FIG. 10 indicates a sine-square waveform generator 72, producing variable frequency wave-forms which are frequency-locked. An amplified sine wave is passed to the audio transducer 28 through an A.C. power amplifier 74. The illumination is controlled through a phase incrementing module 76 receiving waveforms from the generator 72 and causing pulses to be generated suitable for stroboscopic viewing of the eardrum at the desired frequencies. These pulses, the width of which may be varied as required using a variable pulse-width module 78 are amplified in a D.C. power amplifier 80 and then fed to the L.E.D. illumination sources 50. It will be understood that within the dimensional limitations imposed by a patient's auditory meatus it is possible to select from a variety of interchargeable diode arrays having, for example, differing diameters.

In use, the medical practitioner will use the illumination from the diodes 50 to observe a patient's eardrum through the eyepiece by placing the tip of the probe portion 38 into the auditory channel of the patient. The observation may be by steady light, if required, but where the movement of the eardrum is to be observed, will more usually use light pulsed in a stroboscopic manner. Sound emitted at a convenient, desired frequency is directed through the hollow casing 40 and the opening 54 to emerge in a path axially off the annular array of diodes 50. Variations of frequency of light and/or sound may be selected at the discretion of the medical practitioner.

Various modifications may be made within the scope of the invention as claimed in the following claims.

We claim:

1. An optical instrument device capable of permitting viewing of an object or an image thereof, said device comprising an illumination source for providing illumination to assist said viewing, said source being a light-emitting diode, said optical instrument being an auriscope comprising a housing including an illumination source comprising at least one light-emitting diode, a leading probe portion having a substantially tubular configuration, means to provide sound at known frequencies to said probe portion, said probe portion providing an inspection passageway for the tympanum (ear drum) communicating with said housing and means to direct light from said illumination source, in use, onto a tympanum, and means for rendering the light from said source intermittent in a stroboscopic manner, said illumination source including an annular array of said light-emitting diodes surrounding said inspection passageway within said probe portion.

2. A device as claimed in claim 1 wherein said means include reflective surfaces.

3. A device according to claim 1 wherein said leading probe portion is defined by concentric tubes having opposed reflective surfaces, and said array of light-emitting diodes being disposed between said tubes.

4. A device according to claim 1 wherein said leading probe portion is defined by concentric tubes having opposed reflective surfaces, and said array of light-emitting diodes being disposed between said tubes in circumferentially spaced relation.

5. An optical instrument device capable of permitting viewing of an object or an image thereof, said device comprising an illumination source for providing illumination to assist said viewing, said source being a plurality of light-emitting diodes, said optical instrument being an auriscope comprising a housing including an illumination source comprising said plurality of light-emitting diodes, a leading probe portion having a substantially tubular configuration, means to provide sound at known frequencies to said probe portion, said probe portion having an inspection passageway for the tympanum (ear drum) communicating with said housing, and said diodes providing an annular display of light directed in use, onto a tympanum, said annular display of light from said diodes surrounding said inspection passageway within said probe portion.

6. A device according to claim 5, wherein means are provided for deflecting the light emitted from the diode to produce a parallel or substantially parallel beam.

7. An optical instrument device according to claim 5 together with means for rendering light from said diodes intermittent in a stroboscopic manner.

8. An optical instrument device capable of permitting viewing of an object or an image thereof, said device comprising an illumination source for providing illumination to assist said viewing, said source being a light-emitting diode, said optical instrument being an auriscope comprising a housing including an illumination source comprising at least one light-emitting diode, a leading probe portion having a substantially tubular configuration, means to provide sound at known frequencies to said probe portion, said probe portion providing an inspection passageway for the tympanum (ear drum) communicating with said housing and means to direct light from said illumination source, in use, onto a tympanum, said illumination source including an annular array of said light-emitting diodes surrounding said inspection passageway within said probe portion.

9. A device according to claim 8 wherein said leading probe portion is defined by concentric tubes having opposed reflective surface, and said array of light-emitting diodes being disposed between said tubes.

10. A device according to claim 8 wherein said leading probe portion is defined by concentric tubes having opposed reflective surfaces, and said array of light-emitting diodes being disposed between said tubes in circumferentially spaced relation.

* * * * *